(12) United States Patent
Azizi et al.

(10) Patent No.: US 7,322,955 B2
(45) Date of Patent: Jan. 29, 2008

(54) MEDICAMENT INJECTION APPARATUS

(75) Inventors: Mayer Azizi, Basking Ridge, NJ (US); Robert Woolston, Warwick (GB)

(73) Assignee: DCA Design International Limited, Warwick (GB)

( * ) Notice: Subject to any disclaimer, the term of this patent is extended or adjusted under 35 U.S.C. 154(b) by 0 days.

(21) Appl. No.: 10/337,650

(22) Filed: Jan. 8, 2003

(65) Prior Publication Data
US 2003/0153868 A1 Aug. 14, 2003

(30) Foreign Application Priority Data
Jan. 12, 2002 (GB) ................. 0200637.7

(51) Int. Cl.
*A61M 31/00* (2006.01)
(52) U.S. Cl. ...................................... 604/65
(58) Field of Classification Search ............. 604/890.1, 604/891.1, 892.1, 131–134, 151–155, 207–211, 604/236–238
See application file for complete search history.

(56) References Cited

U.S. PATENT DOCUMENTS

| | | | |
|---|---|---|---|
| 4,505,710 A * | 3/1985 | Collins | 604/891.1 |
| 4,560,979 A | 12/1985 | Rosskopf | |
| 5,925,021 A * | 7/1999 | Castellano et al. | 604/207 |
| 6,248,090 B1 * | 6/2001 | Jensen et al. | 604/67 |
| 6,817,986 B2 * | 11/2004 | Slate et al. | 604/68 |

| | | | |
|---|---|---|---|
| 2003/0121813 A1 * | 7/2003 | Juselius | 206/365 |

FOREIGN PATENT DOCUMENTS

| | | |
|---|---|---|
| DE | 198 20 316 A1 | 11/1999 |
| EP | 0 362 484 A2 | 4/1990 |
| WO | WO 97/30742 | 8/1997 |
| WO | WO 99/15214 | 4/1999 |

* cited by examiner

*Primary Examiner*—Catherine S. Williams
(74) *Attorney, Agent, or Firm*—Oliff & Berridge, PLC

(57) ABSTRACT

The present invention relates to a medicament injection apparatus. It is desirable following injection of a medicament to wait a short time before withdrawing the needle unit from the patient to allow injected medicament to disperse within the patient to reduce the risk of some of the injected medicament escaping through the needle wound and so not being dispersed into the patient as desired. This problem is particularly acute where a patient uses the apparatus to self-administer a dose since, where this waiting period is indicated to a user, the waiting period is a set time independent of whether the size of the dose to be injected. The user often feels that for a small dose it is not as important to leave the needle unit within the body for the full waiting period and so does not allow the waiting period properly to elapse. A medicament injection apparatus is disclosed wherein signal means actuated by a processor for signal the end of a predetermined period of time elapsing from the end of the injection operation wherein the predetermined period of time elapsing is dependent upon the amount of the medicament injected. This has as an advantage the giving of a user confidence that the waiting period for each dose size is important and should be respected.

4 Claims, 1 Drawing Sheet

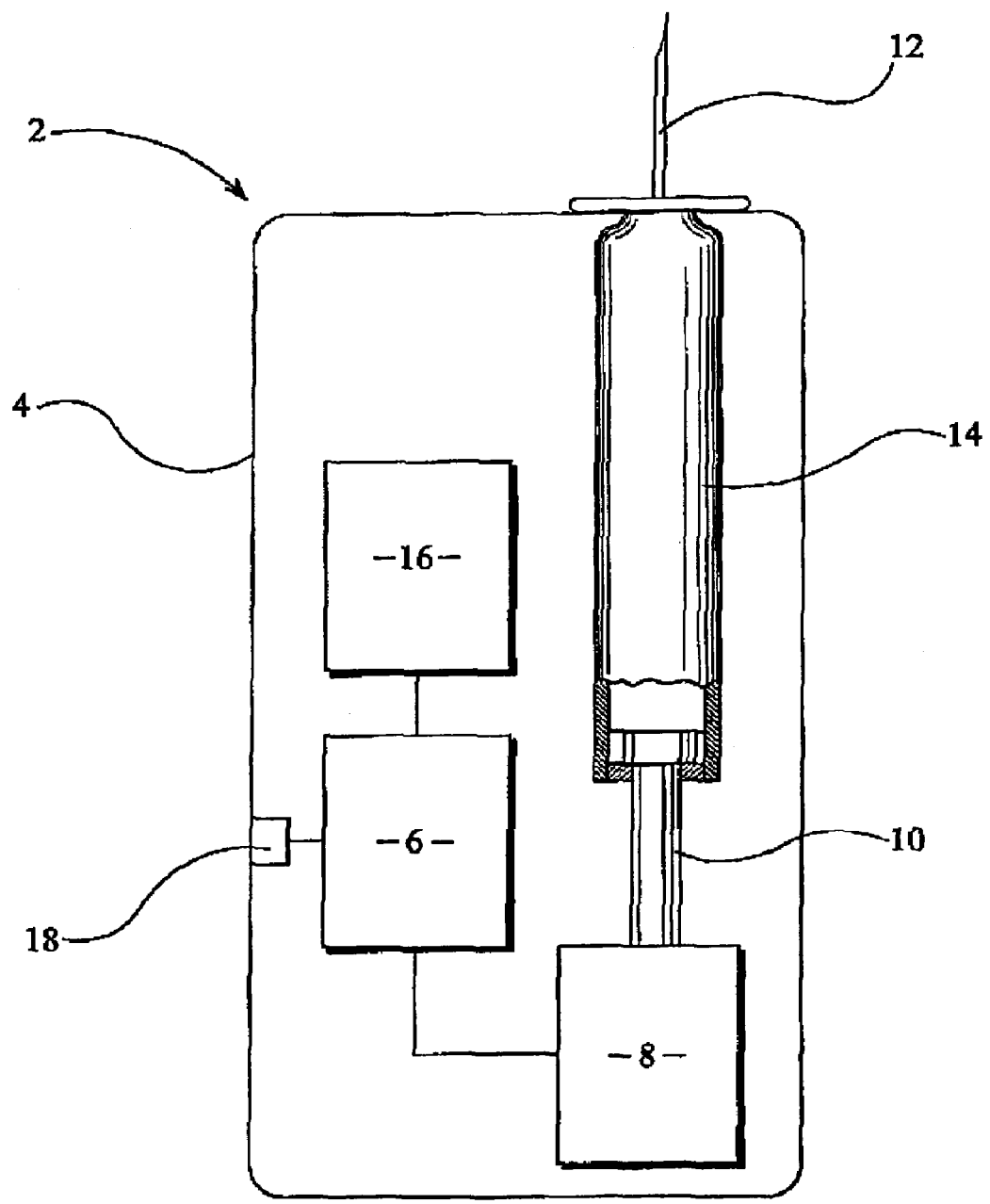

MEDICAMENT INJECTION APPARATUS

FIELD OF THE INVENTION

The present invention relates to a medicament injection apparatus. In particular, but not exclusively, the invention relates to an electronically controlled medicament injection apparatus. A medicament injection apparatus typically comprises means to retain a replaceable medicament cartridge, a needle unit to pierce the medicament cartridge thereby to allow medicament to be expelled from the medicament cartridge and drive means to displace a piston within the medicament cartridge thereby causing the medicament to be expelled.

BACKGROUND TO THE INVENTION

It is desirable following injection of a medicament into a patient to wait a short time before withdrawing the needle unit from the body of the patient. This is because the injected medicament takes a few seconds to disperse locally from the injection site within the body of the patient. If the needle unit is withdrawn too soon after the medicament has been injected, there is a risk that at least some of the injected medicament may escape through the needle wound and not be dispersed into the patient as is desired.

Unfortunately, this problem is particularly acute where a patient uses a medicament injection apparatus to self-administer a medicament. A user may become impatient and withdraw the needle before the medicament has dispersed.

Where this waiting period is indicated to a user, for example by way of display or audible sound in known medicament delivery apparatus, the waiting period is a set time independent of whether the dose size of medicament to be injected is large or small. The user may feel that for a small dose it is not as important to leave the needle unit within the body of the patient for the full waiting period. Unfortunately, it is often the case that the user no longer allows the waiting period to elapse in the belief that the waiting period is not critical.

It is an advantage that the present invention seeks to alleviate this problem.

SUMMARY OF THE INVENTION

According to the present invention, a medicament injection apparatus comprises an injection apparatus for performing an injection operation to inject an amount of medicament, timing means for calculating the time elapsed from an end of the injection operation, a processor and signal means actuated by the processor for signaling the end of a predetermined period of time elapsing from the end of the injection operation wherein the predetermined period of time elapsing is dependent upon the amount of the medicament injected.

This has as an advantage the giving of a user confidence that the waiting period for each dose size is important and should be respected.

Preferably, the predetermined period of time elapsing is proportional to the amount of medicament injected.

Alternatively, the predetermined period of time elapsing is one of a plurality of predetermined values corresponding to a number of different amounts of medicament injected.

BRIEF DESCRIPTION OF THE DRAWING

The invention will now be described by way of example only, with reference to the accompanying drawing, in which:

FIG. 1 shows somewhat schematically a medicament injection apparatus in accordance with the present invention.

DETAILED DESCRIPTION OF THE INVENTION

Referring to the Figure, a schematic arrangement of a medicament injection apparatus according to the present invention is disclosed. The medicament injection apparatus 2 comprises a housing 4, a control unit or microprocessor 6, a drive means 8, a piston 10 and a needle unit 12. The control unit or microprocessor 6 has a timer associated therewith. The medicament injection apparatus 2 may further include a display 16 and/or a sounder 18. The illustrated embodiment shows both. The sounder 18 may conveniently comprise a simple tone emitter or a speech synthesizer.

A medicament cartridge 14, which is preferably replaceable, is located in the medicament injection apparatus between the piston 10 and the needle unit 12. The medicament cartridge 14 includes a closure at a first end adapted to be pierced by the needle unit 12 and a moveable plunger (not shown) located towards a second end of the medicament cartridge 14 and adapted to be driven by a stroke of the piston 10 towards the first end of the medicament cartridge 14.

In use, a dosage of medicament to be injected is set and the needle unit inserted at a suitable location into the patient. The drive means 8 is then actuated to drive the piston 10. The drive means 8 may be actuated mechanically or under the control of the control unit or microprocessor 6. Medicament from within the medicament cartridge 14 is then expelled from the medicament injection apparatus 2.

The timer then calculates the time elapsed from the end of an injection stroke. When a predetermined time has elapsed from the end of the injection stroke, signal means, for example the display 16, the sounder 18 or both, operate under the control of the microprocessor 6 to provide a signal to the user. The user will then understand that the needle unit 12 may then be removed since the medicament should have had sufficient time to disperse.

The predetermined time is dependant upon the amount of medicament chosen to be injected. The value of the predetermined time may be calculated by the microprocessor 6 according to a predetermined functional relationship. Alternatively, the microprocessor 6 may be programmed, for example with a look up table with a number of predetermined values for the predetermined time (the dispersal time) having a correspondence to the possible amounts of medicament that may be injected by the medicament injection apparatus 2.

What is claimed is:

1. A method for injecting an amount of medicament by means of a needle unit of a medicament injection apparatus, comprising:
    a) performing an injection operation by means of a needle unit;
    b) calculating a time elapsed from an end of the injection operation by a timing means; and
    c) actuating a signal means for signaling the end of a predetermined period of time elapsing from the end of the injection operation, wherein the predetermined period of time elapsing is dependent on the amount of medicament injected.

2. The method according to claim 1, wherein the predetermined period of time elapsing is proportional to the amount of medicament injected.

3. The method according to claim 1, wherein the predetermined period of time elapsing is one of a plurality of predetermined values corresponding to a number of different amounts of medicament injected.

4. The method according to claim 1, wherein a processor actuates the signal means.

* * * * *